United States Patent [19]

Shibata et al.

[11] Patent Number: 5,958,084
[45] Date of Patent: *Sep. 28, 1999

[54] OXYALKYLENIZED XANTHANE GUM THICKENERS IN PERMANENT HAIR DYEING COMPOSITIONS AND PROCESSES

[75] Inventors: Yutaka Shibata; Kumi Sugino; Jiro Kawase, all of Tokyo, Japan

[73] Assignee: Kao Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/783,941

[22] Filed: Jan. 21, 1997

[30] Foreign Application Priority Data

Jan. 22, 1996 [JP] Japan .................................. 8-008510

[51] Int. Cl.$^6$ ...................................................... A61K 7/13
[52] U.S. Cl. ...................................................... 8/408; 8/561
[58] Field of Search ............................... 8/406, 407, 408, 8/409, 410, 411, 412, 414, 416, 415, 421, 423, 424, 435, 561; 536/114, 120; 435/104, 910

[56] References Cited

U.S. PATENT DOCUMENTS

| | | | |
|---|---|---|---|
| 3,349,007 | 10/1967 | Schweiger | 536/120 |
| 4,885,006 | 12/1989 | Grollier et al. | 8/423 |
| 4,904,275 | 2/1990 | Grollier | 8/408 |
| 4,985,955 | 1/1991 | Grollier et al. | 8/424 |
| 5,021,067 | 6/1991 | Grollier | 8/409 |
| 5,167,669 | 12/1992 | Grollier | 8/423 |
| 5,180,396 | 1/1993 | Grollier et al. | 8/406 |
| 5,180,397 | 1/1993 | Grollier et al. | 8/406 |
| 5,180,399 | 1/1993 | Grollier et al. | 8/423 |
| 5,478,360 | 12/1995 | Grollier et al. | 8/406 |

*Primary Examiner*—Caroline D. Liott
*Attorney, Agent, or Firm*—Oblon, Spivak, McClelland, Maier & Neustadt, P.C.

[57] ABSTRACT

A permanent hair dyeing composition which contains an oxidation dye precursor, a coupler, an oxyalkylenized xanthane gum, and a salt of an inorganic or organic acid, and hair dyeing processes with such compositions.

9 Claims, No Drawings

OXYALKYLENIZED XANTHANE GUM THICKENERS IN PERMANENT HAIR DYEING COMPOSITIONS AND PROCESSES

BACKGROUND OF THE INVENTION a) Field of the Invention

This invention relates to a hair cosmetic composition which has good spreadability, permits easy application to hair, and provides an excellent feeling of use.

b) Description of the Related Art

A hair cosmetic composition is generally added with one or more of various thickening agents with a view to improving the ease in application by preventing running-down and further to reducing irritation to the skin. Employed as such thickening agents are, for example, natural polymers such as xanthan gum and guar gum, semisynthetic polymers such as methylcellulose and ethylcellulose, and synthetic polymers such as polyvinyl alcohol and polyethylene oxide.

Among these, xanthan gum is widely used because it is hardly affected by pH, temperature and the like and exhibits good thickening effect.

Hair cosmetic compositions which contain xanthan gum are however accompanied by the problem that, when they are taken out of bottoms upon use, they become a lump and show poor spreadability, they cannot be easily applied to hair, and the feeling of use is hence significantly impaired. Further, xanthan gum fails to bring about sufficient thickening effect in systems which contain a salt and a solvent at high concentrations.

To cope with the above-described problem, U.S. Pat. No. 3,349,077 discloses that xanthan gum etherified with an alkylene oxide is usable as a thickening agent. This etherified xanthan gum is described in the U.S. patent to be useful for obtaining an alcohol-base high-viscosity gel, but the U.S. patent has no disclosure whatsoever as to whether it would show sufficient thickening effect in other systems.

Among hair cosmetic compositions, hair dye compositions, hair setting compositions, permanent wave compositions and the like generally contain a salt and a solvent at high concentrations. It has therefore been desired to develop a component which can exhibit sufficient thickening effects in these systems.

SUMMARY OF THE INVENTION

An object of the present invention is therefore to provide a hair cosmetic composition, such as a hair dye composition, hair setting composition or permanent wave composition, which has good spreadability, permits easy application, has excellent feeling of use, and shows sufficiently long-lasting thickening effect even if a salt and a solvent are contained at high concentrations.

Under the foregoing circumstances, the present inventors have proceeded with extensive research. As a result, it has been found that use of an oxyalkylenized xanthan gum as a thickening agent in a system containing an oxidizing agent, a reducing agent, a film-forming polymer, an oxidation dye, an acid dye or the like—such as a hair dye composition, hair setting composition or a permanent wave composition—in which fully-controlled thickening effect has heretofore been unavailable due to inclusion of a salt and a solvent at high concentrations makes it possible to obtain a hair cosmetic composition having good spreadability, permitting easy application to hair and having an excellent feeling of use, leading to the completion of the present invention.

The present invention therefore provides a hair cosmetic composition, comprising at least one component selected from an oxidizing agent, a reducing agent, a film-forming polymer, an oxidation dye, or an acid dye; and an oxyalkylenized xanthan gum.

The present invention also provides a hair cosmetic composition, comprising at least one component selected from an oxidizing agent, a reducing agent, a film-forming polymer, an oxidation dye, or an acid dye; an oxyalkylenized xanthan gum; and at least one additional component selected from an inorganic acid, an organic acid or a salt thereof.

Further, the present invention also provides a semi-permanent to temporary hair dye composition comprising 0.01 to 5 wt. % of an acid dye and 0.01 to 10 wt. % of an oxyalkylenized xanthan gum, wherein the composition has a pH of from 2 to 5.

The present invention also provides a hair setting composition comprising 0.1 to 10 wt. % of a film-forming polymer and 0.1 to 10 wt. % of an oxyalkylenized xanthan gum, wherein the composition has a pH of from 5 to 8.

Still further, the present invention also provides a permanent wave composition comprising 1 to 10 wt. % of a reducing agent and 0.5 to 5 wt. % of an oxyalkylenized xanthan gum, wherein the composition has a pH of from 4.5 to 9.6.

The present invention also provides a permanent hair dye composition comprising 0.1 to 20 wt. % of an oxidation dye and 0.1 to 5 wt. % of an oxyalkylenized xanthan gum, wherein the composition has a pH of from 6 to 9.5.

Moreover, the present invention also provides a semi-permanent to temporary hair dying process, which comprises applying to hair a composition comprising 0.01 to 5 wt. % of an acid dye and 0.01 to 10 wt. % of an oxyalkylenized xanthan gum, wherein the composition has a pH of from 2 to 5.

The present invention also provides a permanent hair dying process, which comprises applying to hair a composition comprising 0.1 to 20 wt. % of an oxidation dye and 0.1 to 5 wt. % of an oxyalkylenized xanthan gum, wherein the composition has a pH of from 6 to 9.5.

DETAILED DESCRIPTION OF THE INVENTION AND PREFERRED EMBODIMENTS

The oxyalkylenized xanthan gum useful in the practice of the present invention is available by substituting at least some of hydroxyl groups of xanthan gum with (poly)oxyalkylene groups and includes, for example, one represented by the below-described formula. Here, the term "the degree of substitution by (poly)oxyalkylene groups [(poly)oxyalkylene substitution degree]" as used herein means an average number of (poly)oxyalkylene units [—$(C_xH_{2x}O)_y$—H units in the below-described formula] bonded per residual group of constituent unit saccharide of xanthan gum.

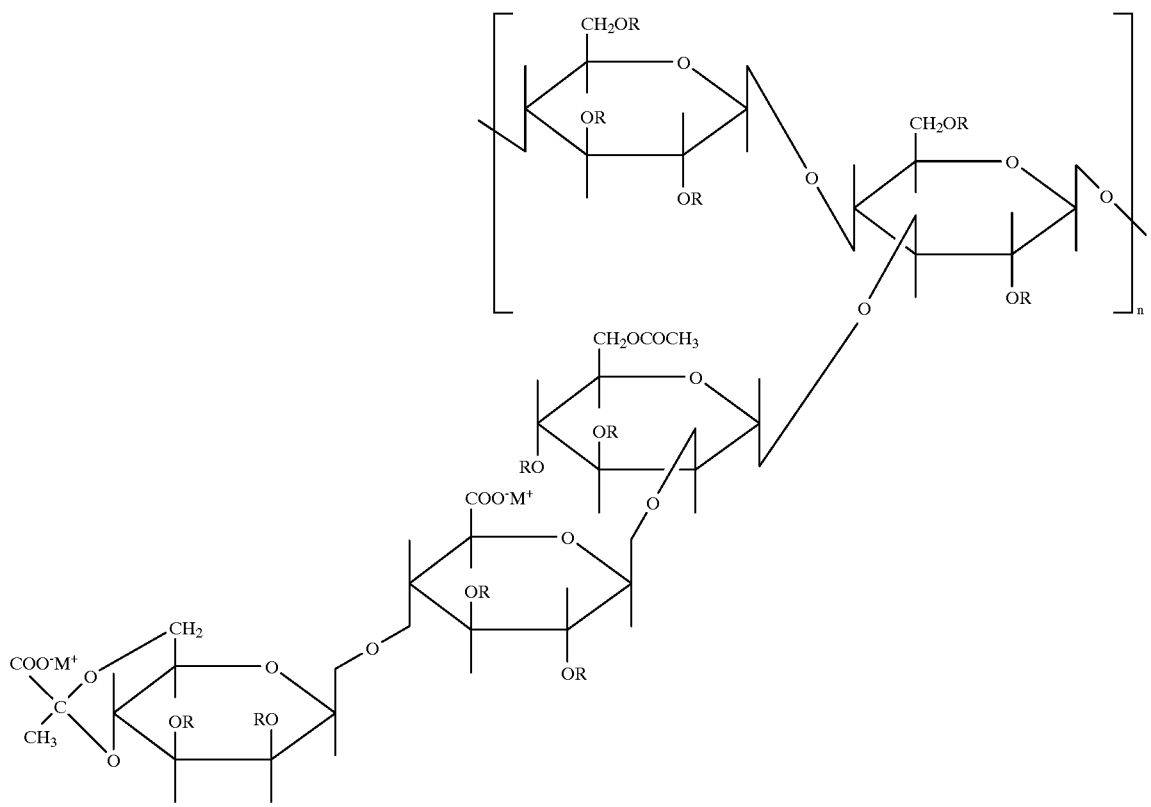

wherein R represents a hydrogen atom of —$(C_xH_{2x}O)_y$—H, x standing for a value of from 1 to 6 and Y denoting a value of from 1 to 20, and $M^+$ represents a metal atom.

Incidentally, each oxyalkylene substitution degree referred to in the present invention means a value determined in accordance with the method subscribed in ASTM D-2367-72.

Preferred examples of the (poly)oxyalkylene group include (poly)oxyalkylene groups having 2–4 carbon atoms, for example, (poly)oxyethylene group, (poly)oxypropylene group and (poly)oxybutylene group.

Such an oxyalkylenized xanthan gum can be prepared, for example, following the process disclosed in U.S. Pat. No. 3,349,077. For example, it can be prepared by mixing xanthan gum with an alkali and a solvent such as water, adding an alkylene oxide and then reacting them to each other. Usable examples of the alkylene oxide include ethylene oxide, propylene oxide, 1-butene oxide and 2-butene oxide. The reaction may preferably be conducted at 40 to 100° C., especially at 60 to 80° C. for 3 to 20 hours.

Regarding the proportions of the alkylene oxide and xanthan gum to be employed in the reaction, it is preferred to determine their proportions so that one or more molecules of the alkylene oxide are added per molecule of xanthan gum. It is possible to adjust the oxyalkylene substitution degree and etherification degree of the resulting oxyalkylenized xanthan gum by modifying their proportions. Incidentally, the term "etherification degree" as used herein means the proportion (%) of hydroxyl groups ether-substituted by (poly)oxyalkylene groups out of the hydroxyl groups in xanthan gum. Xanthan gums having different oxyalkylene substitution degrees and etherification degrees can also be obtained by modifying the reaction time, reaction temperature and the amount of a catalyst.

The oxyalkylene substitution degree of the oxyalkylenized xanthan gum obtained as described above may preferably range from 0.01 to 1.5. In particular, an oxyalkylene substitution degree in a range of from 0.01 to 0.5 provides excellent water solubility and thickening property, while an oxyalkylene substitution degree in a range of from 1 to 1.5 leads to superb solubility in an organic solvent system.

On the other hand, the etherification degree may preferably be from 0.1 to 25%, with a range of from 0.1 to 10% being particularly preferred because this range provides excellent flowability.

Further, at a high etherification degree, a system with an oxyalkylenized xanthan gum incorporated therein has a higher viscosity under acidic condition than under neutral condition when the oxyalkylenized xanthan gum is added in the same amount. At a high substitution degree, on the other, the viscosity is conversely higher under neutral conditions than under acidic conditions when the oxyalkylenized xanthan gum is added in the same amount. By using this property, it is possible to choose an appropriate oxyalkylenized xanthan gum depending on the application.

The etherification degree in the present invention may preferably be determined as follows:

(1) Preparation of a sample solution:

Xanthan gum (0.1 g) is precisely weighed (Wt mg) and poured into a messflask (100 ml). Into the flask is added 1 N sulfuric acid (25 ml), and then the resultant mixture is heated in the water bath to thereby dissolve the xanthan gum. The solution is then cooling down and is added water precisely to adjust the volume of the solution to 100 ml. Thereafter, 4 ml of the solution is placed in a mess flask (20 ml), and is added water to obtain 20 ml of a sample solution.

(2) Preparation of a standard solution:

0.1 g of propylene glycol is weighed precisely (Ws mg), poured into a messflask (100 ml) and is added water to obtain a solution measured precisely as 100 ml. The precisely measured 3 ml of the solution is then placed in a messflask (100 ml) and is added water to thereby obtain a standard solution.

(3) Coloring:

Each 1 ml of the sample solution, the standard solution and water is precisely measured off. Then the three kind of liquids are poured into messflasks (25 ml) separately. Each liquid is allowed to stand for 5 or more minutes in the ice bath. Thereafter, to each liquid, a conc. sulfuric acid (8 ml) is added dropwise while stirring, and subsequently heated precisely for 3 minutes in a water bath. Immediately after the heating, the solutions are cooled down in an ice bath for 10 minutes or more, and then added carefully 0.6 ml of the below-described ninhydrin solution(*) under stirring. The resultant solutions are allowed to stand over 100 minutes in a hot bath at constant temperature of 25±0.5° C. Then, to each of the solutions is added a conc. sulfuric acid to prepare 25 ml solution under stirring.

(4) Measurement:

At 5 minutes after the addition of sulfuric acid, the absorbances (at a wavelenth of 590 nm) of the coloring solutions prepared based on the sample solution, the standard solution, and water (as a control) are measured. The etherification degree is calculated by the equation:

$$\text{The etherification (\%)} = \frac{11.64 \times Ws \times At}{Wt \times As}$$

(wherein Wt is the amont of the sample (mg), Ws is the amount of propylene glycol (mg), At is absorbance of the sample solution and As is absorbance of the standard solution.) (*) Ninhydrin solution used here is prepared by mixing 0.6 g of ninhydrin into 5% of sodium hydrogensulfite solution to obtain 20 ml solution.

In the present invention, it is particularly preferred to use (poly)oxypropylenized xanthan gum which is available by reacting xanthan gum with propylene oxide.

In the hair cosmetic composition according to the present invention, oxyalkylenized xanthan gums can be used either singly or in combination. It is preferred to add one or more oxyalkylenized xanthan gums in a total amount of from 0.01 to 10 wt. % (hereinafter indicated simply by "%") based on the whole composition. In particular, the addition in an amount of from 0.01–5%, notably 0.01 to 3% is preferred as excellent solubility is also brought about.

To the hair cosmetic composition according to the present invention, at least one component selected from an oxidizing agent, a reducing agent, a film-forming polymer, an oxidation dye or an acid dye is added. The addition of at least one component selected from the oxidizing agent, the reducing agent or the oxidation dye out of the above components provides a permanent wave composition, a permanent hair dye composition or the like. On the other hand, the addition of the oxidation dye results in a semi-permanent to temporary hair dye composition. Further, the addition of the film-forming polymer leads to a hair setting composition.

Examples of the reducing agent include thioglycolic acid; thioglycolic acid derivatives; cysteine, N-acylcysteine, and salts thereof; thioglyceryl alkyl ethers; and mercaptoalkylamides. Of these, particularly preferred are thioglycolic acid; glyceryl thioglycolate; L-cysteine, D-cysteine, N-acylcysteine, and the ammonium, quaternary ammonium, and amine (e.g., monoethanolamine, diethanolamine, and triethanolamine) salts of these cysteines; thioglyceryl alkyl ethers such as ethoxyhydroxypropanethiol, methoxyethoxyhydroxypropanethiol, ethoxyethoxyhydroxypropanethiol, and isopropoxyethoxyhydroxypropanethiol; mercaptoethyl propanamide; and mercaptoethylgluconamide.

These reducing agents can be used either singly or in combination. It is preferred to add one or more reducing agents in a total amount of from 0.01 to 15%, especially from 1 to 10% based on the whole composition.

Owing to the addition of such a reducing agent, the hair cosmetic composition according to the present invention can be prepared into a first-package permanent wave composition or the like. To prepare this permanent wave composition, it is preferred to add the reducing agent in an amount of from 1 to 10% and the oxyalkylenized xanthan gum in an amount of from 0.5 to 5% and to adjust the pH to 4.5 to 9.6. When the hair cosmetic composition according to the present invention is provided as a permanent wave composition by the addition of the reducing agent, the set holding property can be improved.

Illustrative of the oxidizing agent are potassium bromate, sodium bromate, sodium perborate and hydrogen peroxide. These oxidizing agent can be added in an amount of from 0.1 to 15%, especially from 5 to 10% based on the whole composition.

By the addition of such an oxidizing agent, the hair cosmetic composition according to the present invention can be provided as a second-package permanent wave composition or a second-package permanent hair dye composition.

Further, examples of the oxidation dye include oxidation dye precursors such as p-phenylenediamine, p-aminophenol, o-phenylenediamine, o-aminophenol, and derivatives thereof. On the other hand, coupling substances which can form various colors when combined with these oxidation dye precursors include, for example, m-pheylenediamine, m-aminophenol, polyhydric phenols and the like.

One or more of these oxidation dye precursors can preferably be added in an amount of from 0.1 to 20%, notably 0.1 to 10% based on the whole composition. Further, one or more of the coupling substances can preferably be added in an amount of from 0.1 to 10%, especially from 0.1 to 5%, as needed, based on the whole composition.

By the addition of such an oxidation dye, the hair cosmetic composition according to the present invention can be provided as a permanent hair dye composition (either as a single-pack type or as a first-package composition of a two-pack type). For the preparation of this permanent hair dye composition, it is preferred to add the oxidation dye in an amount of from 0.1 to 20% and the oxyalkylenized xanthan gum in an amount of from 0.1 to 5% and to adjust the pH to 6 to 9.5.

The addition of the acid dye in the hair cosmetic composition according to the present invention makes it possible to uniformly disperse the dye in a large amount. Hair can therefore be evenly coated with the dye, so that the dyeability can also be improved. No particular limitation is imposed on such an acid dye insofar as it is usable in ordinary cosmetic composition. Illustrative examples of these acid dyes include Red No. 102 (C.I. 16255), Yellow No. 4 (C.I. 19140), Yellow No. 5 (C.I. 15985), Red No. 201 (C.I. 15850), Red No. 227 (C.I. 17200), Orange No. 205 (C.I. 15510), Brown No. 201 (C.I. 20170), Red No. 502 (C.I. 16155), Red No. 503 (C.I. 16150), Red No. 504 (C.I. 14700), Red No. 506 (C.I. 15620), Orange No. 402 (C.I. 14600), Yellow No. 402 (C.I. 18950), Yellow No. 406 (C.I. 14065), Yellow No. 407 (C.I. 18820), Red No. 213 (C.I. 45170), Red No. 214 (C.I. 45170), Red No. 3 (C.I. 45430), Red No. 104(1) (C.I. 45410), Red No. 105(1) (C.I. 45440), Red No. 106 (C.I. 45100), Green No. 2, Green No. 3 (C.I.

42053), Orange N. 207 (C.I. 45425), Yellow No. 202(1) (C.I. 45350), Yellow No. 202(2) (C.I. 45350), Blue No. 202 (C.I. 42052), Blue No. 203 (C.I. 42052), Blue No. 205 (C.I. 42090), Blue No. 2 (C.I. 73015), Yellow No. 203 (C.I. 47005), Blue No. 201 (C.I. 73060), Green No. 201 (C.I. 61570), Blue No. 1 (C.I. 42090), Red No. 230(1) (C.I. 45380), Red No. 231 (C.I. 45410), Red No. 232 (C.I. 45440), Green No. 204 (C.I. 59040), Green No. 205 (C.I. 42095), Red No. 401 (C.I. 45190), Yellow No. 403(1), (C.I. 10316), Green No. 401 (C.I. 10020), Green No. 402 (C.I. 42085), Black No. 401 (C.I. 20470), and Violet No. 401 (C.I. 60730).

These acid dyes can be used either alone or in combination. It is preferred to add one or more of them in an amount of from 0.001 to 10%, especially from 0.01 to 5% based on the whole composition.

To provide such a semi-permanent to temporary hair dye composition, it is preferred to add the acid dye in an amount of from 0.01 to 5% and the oxyalkylenized xanthan gum in an amount of 0.01 to 10% and to adjust the pH to 2 to 5.

The addition of the film-forming polymer to the hair cosmetic composition according to the present invention provides a hair setting composition having excellent film characteristics. Examples of such a film-forming polymer include the following polymers (1) to (8):

(1) Polyvinylpyrrolidone-base high polymers:
Polyvinylpyrrolidones:
Commercial products include "Luviskol K12" and "Luviskol K30" (trade names, products of BASF AG); and "PVP K15" and "PVP K30" (trade names, products of International Specialty Products, Inc.).

Polyvinylpyrrolidone/vinyl acetate copolymers:
Commercial products include "Luviskol VA28" and "Luviskol VA73" (trade names, products of BASF AG); "PVP/VA E-735" and "PVP/VA S-630)" (trade names, products of International Specialty Products, Inc.).

Polvinylpyrrolidone/vinyl acetate/vinyl propionate terpolymers:
Commercial products include "Luviskol VAP343" (trade name, product of BASF AG).

Polyvinylpyrrolidone/alkyl aminoacrylate copolymers:
Commercial products include "Luviflex" (trade name, product of BASF AG); and "Copolymer 845", "copolymer 937" and "Copolymer 958" (trade names, products of International Specialty Products, Inc.).

Polyvinylpyrrolidone/acrylate/(meth)acrylic acid copolymers:
Commercial products include "Luviflex VBM35" (trade name, product of BASF AG).

Polyvinylpyrrolidone/alkyl aminoacrylate/vinyl caprolactam:
Commercial products include "Copolymer VC-713" (trade name, products of International Specialty Products, Inc.).

(2) Acidic-vinyl-ether-base high polymers:
Methyl vinyl ether/alkyl half ester of maleic anhydride copolymers:
Commercial products include "Gantrez ES-225", "Gantrez ES-425" and "Gantrez SP-215" (trade names, products of International Specialty Products, Inc.).

(3) Acidic-polyvinyl-acetate-base high polymers:
Vinyl acetate/crotonic acid copolymers:
Commercial products include "Resin 28-1310" (trade name, product of National Starch Company); and "Luviset CA66" (trade name; product of BASF AG).

Vinyl acetate/crotonic acid/vinyl neodecanoate copolymers:

Commercial products include "Resin 28-2930" (trade name, product of National Starch Company).

Vinyl acetate/crotonic acid/vinyl propionate copolymers:
Commercial products include "Luviset CAP" (trade name, product of BASF AG).

(4) Acidic acrylic high polymers:
(Meth)acrylic acid/(meth)acrylate ester copolymers:
Commercial products include "TPlascize L53P" (trade name, product of GOO CHEMICAL Co., Ltd.); and "Diahold" (trade name, product of Mitsubishi Chemical Corporation).

Acrylic acid/alkyl acrylate/alkylacrylamide copolymers:
Commercial products include "Ultrahold 8" (trade name, product of BASF AG); "Amphomer V-42" (trade name, product of National Starch Company).

(5) Amphoteric acrylic high polymers:
(Meth)acrylethylbetaine/alkyl (meth)acrylate copolymers:
Examples include copolymers of N-methacryloyloxyethyl N,N-dimethylammonium α-N-methylcarboxybetaine and alkyl (meth)acrylates. Commercial products include "Yukaformer M-75" and "Yukaformer SM" (trade names, product of Mitsubishi Chemical Corporation).

Alkyl acrylate/butylaminoethyl metharylate/octylacrylamide copolymers:
Examples include octylacrylamide/acrylate/butylaminoethyl methacrylate copolymer. Commercial products include "Amphomer 28-4910" (trade name, product of National Starch Company).

(6) Basic acrylic high polymers:
Acrylamide-acrylate ester tetrapolymers:
Examples include those disclosed in Japanese Patent Application Laid-Open (Kokai) No. HEI 2-180911.

(7) Cellulose derivatives:
Cationic cellulose derivatives:
Commercial products include "Celquat H-100" and "Celquat L-200" (trade names, products of National Starch Company).

(8) Chitin and chitosan derivatives:
Hydroxypropylchitosan
Commercial products include "Chitofilmer" (trade name, product of Ichimaru Pharcos Co., Ltd.

Salts of carboxymethyl chitin, carboxymethyl chitosan or chitosan and a monocarboxylic acid such as pyrrolidonecarboxylic acid, lactic acid or glycolic acid or dicarboxylic acid such as adipic acid or succinic acid:
Commercial products include "Chimer PC" (pyrrolidonecarboxylate salt) and "Chitomer L" (oxalate salt) (trade names, product of Union Carbide Corporation).

Of these film-forming polymers, particularly preferred are polyvinylpyrrolidone-base high polymers, acidic-vinyl-ether-base high polymers, acidic-polyvinyl-acetate-base high polymers, acidic acrylic high polymers, and amphoteric acrylic high polymers. These film-forming polymers can be used either alone or in combination. It is preferred to add the film-forming polymer in an amount of from 0.1 to 1.0%, especially from 0.5 to 5% based on the whole composition.

To prepare such a hair setting composition, it is preferred to add the film-forming polymer in an amount of from 0.1 to 10% and the oxyalkylenized xanthan gum in an amount of from 0.1 to 10% and to adjust the pH to 5 to 8.

Owing to the addition of the oxyalkylenized xanthan gum, the hair cosmetic composition according to the present invention has good spreadability, permits easy application and provides excellent feeling of use. Further, sufficient thickening effect can be obtained. Sufficient thickening effect can be continuously retained even in systems where conventional thickening agents have difficulty to achieve thickening, especially even in systems where a salt and a solvent are contained at high concentrations.

Here, the salt usable for incorporation in the hair cosmetic composition according to the present invention can be any one of inorganic salts, organic salts, polymer electrolytes and the like which are employed in general hair cosmetic compositions. Illustrative examples include sodium salts, potassium salts, ammonium salts, and alkanolamine salts (e.g., triethanolamine salts) of inorganic acids, such as phosphoric acid, sulfuric acid and nitric acid, and organic acids such as citric acid, glycolic acid, succinic acid, tartaric acid, lactic acid, fumaric acid, malic acid, levulinic acid, butyric acid, valeric acid, oxalic acid, maleic acid and mandelic acid.

Illustrative of such polymer electrolytes are water-soluble sodium sulfonate of polyester, sodium poly (styrenesulfonate), poly(meth)acrylates, polymaleates and polyphosphates.

These salts can be used either singly or in combination. One or more of these salts can be added preferably in an amount of from 0.1 to 20%, especially from 0.1 to 10%, specifically from 1 to 8% based on the whole composition.

No particular limitation is imposed on the solvent usable for incorporation in the hair cosmetic composition according to the present invention, insofar as it is usable in ordinary hair cosmetic compositions. Illustrative examples include monohydric alcohols containing $C_{1-6}$ alkyl groups such as ethanol, 1-propanol, 2-propanol, isopropanol, 1-butanol and 2-butanol; dihydric or polyhydric alcohols containing $C_{3-8}$ alkyl groups such as propanediol, butanediol, pentanediol, hexanediol, hexantriol, heptanediol, heptanetriol, octanediol, octanetriol, isoprene glycol, propylene glycol, glycerin, diethylene glycol monoethyl ether, diethylene glycol diethyl ether, and ethylene glycol monoethyl ether; N-alkylpyrrolidones in liquid forms at room temperature, such as N-methyl-2-pyrrolidone, N-ethyl-2-pyrrolidone, N-propyl-2-pyrrolidone, N-butyl-2-pyrrolidone, and N-cyclohexyl-2-pyrrolidone; lower alkylene carbonates such as ethylene carbonate and propylene carbonate; aromatic alcohols such as benzyl alcohol, cinnamyl alcohol, p-anisyl alcohol, p-methylbenzyl alcohol, phenoxyethanol, phenoxyisopropanol, 2-benzylethanol, and β-phenylethyl alcohol.

These solvents can be used either singly or in combination. One or more of these solvents can be added preferably in an amount of from 0.1 to 60% based on the whole composition. Especially, an amount of from 0.1 to 50%, specifically from 0.1 to 30% is preferred because sufficient spreadability and thickening effect can be obtained.

To provide the hair cosmetic composition according to the present invention as a permanent wave composition, it is preferred to add the oxyalkylenized xanthan gum in an amount of from 0.5 to 5%, the salt in an amount of from 0.5 to 5%, the solvent in an amount of from 0 to 5% and the reducing agent in an amount of from 1 to 10% and also to adjust the pH of from 4.5 to 9.6.

Further, to provide the hair cosmetic composition according to the present invention as a permanent hair dye composition, it is preferred to add the oxyalkylenized xanthan gum in an amount of from 0.1 to 5%, the salt in an amount of from 0.1 to 5%, the solvent in an amount of from 0 to 30% and the oxidation dye in an amount of 0.1 to 20% and also to adjust the pH of from 6 to 9.5.

To provide the hair cosmetic composition according to the present invention as a semi-permanent to temporary hair dye composition, it is preferred to add the oxyalkylenized xanthan gum in an amount of from 0.01 to 10%, the salt in an amount of from 0.1 to 20%, the solvent in an amount of from 3 to 50% and the acid dye in an amount of 0.01 to 5% and also to adjust the pH of from 2 to 5.

To provide the hair cosmetic composition according to the present invention as a temporary hair-setting composition, it is preferred to add the oxyalkylenized xanthan gum in an amount of from 0.1 to 10%, the salt in an amount of from 0.01 to 1%, the solvent in an amount of from 0.5 to 30% and the film-forming polymer in an amount of 0.1 to 5% and also to adjust the pH to 5 to 8.

To the hair cosmetic composition according to the present invention, components employed in ordinary hair cosmetic compositions can be added as desired in addition to the above-described components to extents not impairing the advantageous effects of the present invention. Illustrative of such additional components are surfactants such as cationic surfactants, anionic surfactants and nonionic surfactants; higher alcohols containing linear or branched, alkyl or alkenyl groups; hydrocarbons such as liquid paraffin and vaseline; liquid lanolin, and lanolin derivatives such as lanolin fatty acids; phospholipids such as lecithin; sterols such as cholesterol, and derivatives thereof; collagen-degraded peptide derivatives; perfluoropolyethers; oils and fats, such as higher alcohol-higher fatty acid esters, higher fatty acids, and alkyl- or alkenyl-containing, long-chain amide amines; animal or vegetable oils and fats such as mink oil and olive oil; medicinally-effective ingredients such as anti-dandruff agents, disinfectants and vitamins; antiseptics such as parabens; coloring matters such as dyes and pigments; ultraviolet light absorbers; plant extracts; astringents; perfume bases; and colors.

The hair cosmetic composition according to the present invention can be prepared by a method known per se in the art. No particular limitation is imposed on its form, and it can be prepared into a hair setting composition, a temporary hair dye composition, a permanent hair dye composition, a permanent wave composition or the like by using various components, such as those described above, in combination as needed depending on the application purpose.

The hair cosmetic composition according to the present invention has good spreadability, permits easy application to hair and gives excellent feeling of use. Further, even in a system containing a salt and a solvent at high concentrations, sufficient thickening effect remains.

The present invention will next be described in further detail by the following Examples. It should however be borne in mind that the present invention is not limited to or by them.

PRODUCTION EXAMPLE 1

To a closed reaction vessel equipped with a stirrer, 200 g of xanthan gum ("Keltol", trademark; product of Kelco Company), 8 g of sodium hydroxide, 12 g of methanol and 4 g of water were added. They were mixed under stirring for about 1 hour at room temperature. Propylene oxide (80 g) was added to the resultant mixture, followed by a reaction at 70–75° C. for 4 hours. The reaction mixture was allowed to cool down to room temperature and was then neutralized with concentrated sulfuric acid. The resulting solid matter was dried and ground, whereby 225 g of oxypropylenized xanthan gum powder were obtained. The oxypropylene substitution degree and etherification degree of the oxypropylenized xanthan gum were 0.05 and 1.5 (%), respectively.

PRODUCTION EXAMPLE 2

To a closed reaction vessel equipped with a stirrer, 200 g of xanthan gum ("Kelsan", trademark; product of Kelco Company), 16 g of sodium hydroxide, 24 g of methanol and 8 g of water were added. They were mixed under stirring for about 1 hour at room temperature. After the mixture was allowed to stand overnight, 80 g of propylene oxide were added, followed by a reaction at 70–75° C. for 4 hours. The reaction mixture was allowed to cool down to room temperature and was then neutralized with concentrated sulfuric acid. The resulting solid matter was dried and ground, whereby 259 g of oxypropylenized xanthan gum powder were obtained. The oxypropylene substitution degree and etherification degree of the oxypropylenized xanthan gum were 0.15 and 3.7 (%), respectively.

PRODUCTION EXAMPLE 3

To a closed reaction vessel equipped with a stirrer, 200 g of xanthan gum ("Keltol", trademark; product of Kelco Company), 12 g of sodium hydroxide, 18 g of methanol and 6 g of water were added. They were mixed under stirring for about 1 hour at room temperature. Propylene oxide (120 g)

A: The viscosity was 500 cp or higher.

B: The viscosity was 100 cp or higher but lower than 500 cp.

C: The viscosity was lower than 100 cp.

(2) Flowability:

Each hair dye composition was placed to a height of 10 cm in a glass tube of 5 cm in diameter and 20 cm in height. After the hair dye composition thoroughly shaken up and down at room temperature for 30 seconds, the hair dye composition was left over for 1 minute. The glass tube was then caused to fall down sideways over 90 degrees. Ten (10) seconds later, the surface smoothness of the hair dye composition was ranged in accordance with the following standards.

A: The surface was smooth.

B: The surface was not smooth.

TABLE 1

| Component (%) | Invention product 1 | Comparative product | | | | | | | | |
|---|---|---|---|---|---|---|---|---|---|---|
| | | 1 | 2 | 3 | 4 | 5 | 6 | 7 | 8 | 9 |
| Oxypropylenized xanthan gum (Pro. Ex. 1) | 1 | — | — | — | — | — | — | — | — | — |
| Xanthan gum | — | 1 | — | — | — | — | — | — | — | — |
| Hydroxyethylcellulose | — | — | 1 | — | — | — | — | — | — | — |
| Hydroxypropylcellulose | — | — | — | 1 | — | — | — | — | — | — |
| Cationized cellulose | — | — | — | — | 1 | — | — | — | — | — |
| Tragacanth gum | — | — | — | — | — | 1 | — | — | — | — |
| Tamarind polysaccharide | — | — | — | — | — | — | 1 | — | — | — |
| Guar gum | — | — | — | — | — | — | — | 1 | — | — |
| Kimiloid | — | — | — | — | — | — | — | — | 1 | — |
| Polyvinyl alcohol | — | — | — | — | — | — | — | — | — | 1 |
| Benzyl alcohol | 3 | 3 | 3 | 3 | 3 | 3 | 3 | 3 | 3 | 3 |
| Citric acid | 4 | 4 | 4 | 4 | 4 | 4 | 4 | 4 | 4 | 4 |
| Sodium hydroxide | q.s.* | q.s.* | q.s.* | q.s.* | q.s.* | q.s.* | q.s.* | q.s.* | q.s.* | q.s.* |
| Ethanol | 15 | 15 | 15 | 15 | 15 | 15 | 15 | 15 | 15 | 15 |
| Black No. 401 | 0.03 | 0.03 | 0.03 | 0.03 | 0.03 | 0.03 | 0.03 | 0.03 | 0.03 | 0.03 |
| Violet No. 401 | 0.04 | 0.04 | 0.04 | 0.04 | 0.04 | 0.04 | 0.04 | 0.04 | 0.04 | 0.04 |
| Orange No. 205 | 0.03 | 0.03 | 0.03 | 0.03 | 0.03 | 0.03 | 0.03 | 0.03 | 0.03 | 0.03 |
| Purified water | Balance | Balance | Balance | Balance | Balance | Balance | Balance | Balance | Balance | Balance |
| Viscosity immediately after preparation | A | A | A | A | A | A | A | A | A | C |
| Viscosity one month after preparation | A | A | C | C | C | C | C | C | C | C |
| Flowability | A | B | A | A | A | B | B | B | A | A |

*Quantity sufficient to adjust the pH to 3.

was added to the resultant mixture, followed by a reaction at 70–75° C. for 5 hours. The reaction mixture was allowed to cool down to room temperature and was then neutralized with concentrated sulfuric acid. The resulting solid matter was dried and ground, whereby 265 g of oxypropylenized xanthan gum powder were obtained. The oxypropylene substitution degree and etherification degree of the oxypropylenized xanthan gum were 0.23 and 6.3 (%), respectively.

EXAMPLE 1

Semi-permanent hair dye compositions of the formulations shown in Table 1 were prepared by a method known per se in the art, and their viscosities and flowabilities were ranked. The results are also presented in Table 1.

(Ranking methods)

(1) Viscosity:

The viscosity of each semi-permanent hair dye composition was measured at 30° C. by a Brookfield type viscometer (No. 4, 30 rpm) immediately after its preparation and after stored at 40° C. for 1 month. The measurement data were ranked in accordance with the following standards.

EXAMPLE 2

Gel-lotion-type styling compositions of the formulations shown in Table 2 were prepared by a method known per se, and their viscosities immediately after the preparation were measured in the same manner as in Example 1. Further, their hair-setting abilities were ranked by the below-described method. The results are shown in Table 2.

(Ranking method)

Hair-setting ability:

A bundle of hair of 18 cm in length and 1.5 g in weight was wetted with water. After towel-drying, each styling composition was applied to the hair in an amount of 2 g. The thus-coated hair was wound around a rod of 2 cm in diameter and was then allowed to naturally dry up. After the hair became dry, the curled hair was taken out of the rod. The curled hair was suspended for 30 minutes in a constant-temperature chamber (20° C., 98% R.H.). Uncurling of the hair was observed. The hair-setting ability was then ranged in accordance with the following standards.

A: Good hair-setting ability.
B: Average hair-setting ability.
C: Poor hair-setting ability.

TABLE 2

| Component (%) | Invention product | | | | Comp. product | |
|---|---|---|---|---|---|---|
| | 2 | 3 | 4 | 5 | 10 | 11 |
| Oxypropylenized xanthan gum (etherification degree: 15%) | 1 | — | — | — | — | — |
| Oxypropylenized xanthan gum (etherification degree: 9%) | — | 1 | — | — | — | — |
| Oxypropylenized xanthan gum (etherification degree: 4.22%) | — | — | 1 | — | — | — |
| Oxypropylenized xanthan gum (etherification degree: 3.9%) | — | — | — | 1 | — | — |
| Xanthan gum | — | — | — | — | 1 | 1 |
| Monoethanolamine | 3 | 3 | 3 | 3 | 3 | 3 |
| Ethanol | 50 | 50 | 50 | 50 | 50 | 10 |
| Water | 46 | 46 | 46 | 46 | 46 | 46 |
| Viscosity (cp) | 1100 | 1000 | 1080 | 492 | 0 | 65 |
| Hair-setting ability | A | A | A | A | C | B |

EXAMPLE 3

First-package permanent wave compositions of the formulations shown in Table 3 were prepared by a method known per se in the art, and their viscosities immediately after the preparation were measured in the same manner as in Example 1. The results are shown in Table 3.

TABLE 3

| Component (%) | Inventive product | | Comparative product | |
|---|---|---|---|---|
| | 6 | 7 | 12 | 13 |
| Hexylene glycol | 40 | 40 | 40 | 40 |
| N-acetylcysteine | 8.5 | 8.5 | 8.5 | 8.5 |
| Thioglycolic acid | 0.9 | 0.9 | 0.9 | 0.9 |
| Monoethanolamine | 5 | 5 | 5 | 5 |
| Oxypropylenized xanthan gum (etherification degree: 9%) | 3 | — | — | — |
| Oxypropylenized xanthan gum (etherification degree: 19.5%) | — | 3 | — | — |
| Xanthan gum | — | — | 3 | — |
| Carboxyvinyl polymer ("Carbopole 940", trade name; product of B. F. Goodrich Company) | — | — | — | 3 |
| Water | Balance | Balance | Balance | Balance |
| pH | 9.0 | 9.0 | 9.0 | 9.0 |
| Viscocity (cp) | 1500 | 2000 | Separated | Separated |

We claim:

1. A permanent hair dyeing composition, comprising:
   an oxidation dye precursor:
   a coupler;
   0.01 to 10 wt. % of an oxyalkylenized xanthane gum; and
   0.1 to 20 wt. % of a salt of an inorganic acid or an organic acid.

2. A hair dyeing composition according to claim 1, wherein said oxyalkylenized xanthan gum is one available by (poly)oxyalkyleneetherifying at least some of hydroxyl groups of xanthan gum.

3. A hair dyeing composition according to claim 1, wherein (poly)oxyalkylene groups of said oxyalkylenized xanthan gum are (poly)oxyalkylene groups having 2 to 4 carbon atoms.

4. A hair dyeing composition according to claim 1, wherein said oxyalkylenized xanthan gum has an oxyalkylene substitution degree of from 0.01 to 1.5 and an etherification degree of from 0.1 to 25%.

5. A hair dyeing composition according to claim 1, wherein said oxyalkylenized xanthan gum has an oxyalkylene substitution degree of from 0.03 to 0.5 and an etherification degree of from 1 to 20%.

6. A hair dyeing composition according to claim 1, wherein said oxyalkylenized xanthan gum has an oxyalkylene substitution degree of from 0.05 to 0.3 and an etherification degree of from 2 to 10%.

7. A hair dyeing composition according to claim 1, wherein said oxyalkylenized xanthan gum is contained in an amount of 0.01 to 5 wt. %.

8. A permanent hair dye composition comprising 0.1 to 20 wt. % of an oxidation dye precursor, a coupler, 0.1 to 5 wt. % of an oxyalkylenized xanthan gum, and 0.1 to 20 wt. % of a salt of an inorganic acid or an organic acid, wherein the composition has a pH of from 6 to 9.5.

9. A permanent hair dyeing process, which comprises applying to hair a composition comprising 0.1 to 20 wt. % of an oxidation dye precursor, a coupler, 0.1 to 20 wt. % of a salt of an inorganic acid or an organic acid, and 0.1 to 5 wt. % of an oxyalkylenized xanthane gum, wherein the composition has a pH from 6 to 9.5.

* * * * *